(12) United States Patent
Banco et al.

(10) Patent No.: US 10,010,638 B2
(45) Date of Patent: Jul. 3, 2018

(54) WAX MELT WITH FILLER

(71) Applicant: S. C. JOHNSON & SON, INC., Racine, WI (US)

(72) Inventors: Michael J. Banco, Racine, WI (US); Michael J. Fischer, Kenosha, WI (US); Deborah Holmes Parker, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 73 days.

(21) Appl. No.: 15/181,641

(22) Filed: Jun. 14, 2016

(65) Prior Publication Data

US 2017/0354752 A1 Dec. 14, 2017

(51) Int. Cl.
*A61L 9/012* (2006.01)
*A61L 9/00* (2006.01)
*C11C 5/00* (2006.01)

(52) U.S. Cl.
CPC ............. *A61L 9/012* (2013.01); *A61L 9/00* (2013.01); *C11C 5/002* (2013.01)

(58) Field of Classification Search
CPC ..................................................... A61L 9/012
See application file for complete search history.

(56) References Cited

U.S. PATENT DOCUMENTS

| | | |
|---|---|---|
| 1,954,659 A | 4/1934 | Will |
| 2,422,990 A | 6/1947 | Benjamin |
| 2,434,557 A | 1/1948 | Fox, Jr. et al. |
| 2,439,506 A | 4/1948 | Christian |
| 2,461,723 A | 2/1949 | Cowan |
| 3,002,221 A | 10/1961 | Arthur |
| 3,324,034 A | 6/1967 | Merz et al. |
| 3,417,040 A | 12/1968 | Kremer |
| 3,519,586 A | 7/1970 | Combs et al. |
| 3,556,403 A | 1/1971 | Manginelli |
| 3,630,697 A | 12/1971 | Cassar et al. |
| 3,680,995 A | 8/1972 | Frazier, Jr. et al. |
| 3,698,640 A | 10/1972 | Stanciu |
| 3,702,495 A | 11/1972 | Renoe |
| 3,779,785 A | 12/1973 | Stiles et al. |
| 3,804,744 A | 4/1974 | Fera |

(Continued)

FOREIGN PATENT DOCUMENTS

| | | |
|---|---|---|
| EP | 706789 A1 | 4/1996 |
| EP | 723776 A1 | 7/1996 |

(Continued)

OTHER PUBLICATIONS

WPI World Patent Information Derwent, vol. 13. No. 81, Feb. 5, 1981, XP002091977, 1 page.

(Continued)

*Primary Examiner* — Arrie L Reuther
(74) *Attorney, Agent, or Firm* — Quarles & Brady LLP

(57) ABSTRACT

A wax melt includes between about one and about sixty percent by weight of paraffin wax, between about 3 percent and about 20 percent by weight of fragrance, and between about 10 percent and about 35 percent by weight of a silicate. The silicate causes between about 97 percent and about 98 percent of a wax melt weight to be retained over a time period of about sixteen hours when maintained at about sixty-five degrees Celsius.

3 Claims, 4 Drawing Sheets

(56) References Cited

U.S. PATENT DOCUMENTS

| | | | |
|---|---|---|---|
| 3,841,813 | A | 10/1974 | Stanciu |
| 3,998,922 | A | 12/1976 | Weiss |
| 4,002,706 | A | 1/1977 | Pretorius |
| 4,017,231 | A | 4/1977 | Karlsson |
| 4,110,261 | A | 8/1978 | Newland |
| 4,396,673 | A | 8/1983 | Ball et al. |
| 4,405,509 | A | 9/1983 | Rogers et al. |
| 4,446,087 | A | 5/1984 | Templin |
| 4,515,909 | A | 5/1985 | Sawano et al. |
| 4,614,625 | A | 9/1986 | Wilson |
| 4,714,496 | A | 12/1987 | Luken, Jr. et al. |
| 4,813,975 | A | 3/1989 | Poulina et al. |
| 4,934,921 | A | 6/1990 | Shieh |
| 4,948,359 | A | 8/1990 | Yasui |
| 4,971,547 | A | 11/1990 | Nett, Jr. et al. |
| 5,037,874 | A | 8/1991 | Nuttens et al. |
| 5,066,216 | A | 11/1991 | Kowtko et al. |
| 5,205,969 | A | 4/1993 | Nett, Jr. et al. |
| 5,294,251 | A | 3/1994 | Urena |
| 5,578,089 | A | 11/1996 | Elmastoy |
| 5,773,039 | A | 6/1998 | Jones |
| 5,861,128 | A | 1/1999 | Vick et al. |
| 5,869,555 | A | 2/1999 | Simmons et al. |
| 5,916,949 | A | 6/1999 | Shapero |
| 5,919,423 | A | 7/1999 | Requejo et al. |
| 5,955,034 | A | 9/1999 | Zaunbrecher |
| 5,959,129 | A | 9/1999 | van Dam et al. |
| 5,972,319 | A | 10/1999 | Linn et al. |
| 6,019,804 | A | 2/2000 | Requejo et al. |
| 6,036,925 | A | 3/2000 | Adams et al. |
| 6,063,144 | A | 5/2000 | Caldaza et al. |
| 6,086,644 | A | 7/2000 | Nakatsu et al. |
| 6,106,597 | A | 8/2000 | Starks et al. |
| 6,110,880 | A | 8/2000 | VerStrate |
| 6,111,055 | A | 8/2000 | Berger et al. |
| 6,129,771 | A | 10/2000 | Ficke et al. |
| 6,214,918 | B1 | 4/2001 | Johnson |
| 6,224,641 | B1 | 5/2001 | Matzat et al. |
| 6,267,970 | B1 | 7/2001 | Matesevac |
| 6,284,007 | B1 | 9/2001 | Tao |
| 6,306,353 | B2 | 10/2001 | Freeman et al. |
| 6,380,462 | B1 | 4/2002 | Kridl |
| 6,428,753 | B2 | 8/2002 | Freeman |
| 6,440,349 | B1 | 8/2002 | Johnson |
| 6,497,735 | B2 | 12/2002 | Tao |
| 6,500,218 | B1 | 12/2002 | Fan |
| 6,503,077 | B2 | 1/2003 | Orth et al. |
| 6,503,285 | B1 | 1/2003 | Murphy |
| 6,533,828 | B1 | 3/2003 | Calzada |
| 6,544,303 | B2 | 4/2003 | Calzada |
| 6,599,334 | B1 | 7/2003 | Anderson |
| 6,623,855 | B2 | 9/2003 | Hsia |
| 6,645,261 | B2 | 11/2003 | Murphy et al. |
| 6,730,137 | B2 | 5/2004 | Pesu et al. |
| 6,755,641 | B1 | 6/2004 | Nakanishi |
| 6,758,869 | B2 | 7/2004 | Roeske |
| 6,770,104 | B2 | 8/2004 | Murphy |
| 6,773,469 | B2 | 8/2004 | Murphy |
| 6,776,808 | B2 | 8/2004 | Foster |
| 6,797,020 | B2 | 9/2004 | Murphy |
| 6,805,855 | B2 | 10/2004 | Mattai et al. |
| 6,824,572 | B2 | 11/2004 | Murphy |
| 6,852,140 | B1 | 2/2005 | Roeske |
| 7,018,432 | B2 | 3/2006 | Moussouni |
| 7,086,852 | B2 | 8/2006 | Nakanishi |
| 7,128,766 | B2 | 10/2006 | Murphy et al. |
| 7,148,284 | B2 | 12/2006 | Morrison et al. |
| 7,160,337 | B2 | 1/2007 | Williams et al. |
| 7,192,457 | B2 | 3/2007 | Murphy et al. |
| 7,217,301 | B2 | 5/2007 | Murphy et al. |
| 7,220,288 | B2 | 5/2007 | D'Amico et al. |
| 7,259,219 | B2 | 8/2007 | Rosen et al. |
| 7,267,743 | B2 | 9/2007 | Borsinger et al. |
| 7,291,187 | B2 | 11/2007 | Welch et al. |
| 7,294,189 | B2 | 11/2007 | Wantling |
| 7,335,372 | B2 | 2/2008 | Hannich et al. |
| 7,387,649 | B2 | 6/2008 | Tao |
| 7,410,513 | B2 | 8/2008 | Requejo et al. |
| 7,420,008 | B2 | 9/2008 | Bloom |
| 7,445,648 | B2 | 11/2008 | Hudson et al. |
| 7,449,504 | B2 * | 11/2008 | Richter ............... C08L 23/02 523/205 |
| 7,462,205 | B2 | 12/2008 | Murphy |
| 7,510,584 | B2 | 3/2009 | Cap |
| 7,549,396 | B2 | 6/2009 | Hurwitz et al. |
| 7,569,084 | B2 | 8/2009 | Tao et al. |
| 7,588,607 | B1 | 9/2009 | Cap |
| 7,601,184 | B2 | 10/2009 | Tischendorf |
| 7,637,968 | B2 | 12/2009 | Murphy |
| 7,671,122 | B2 | 3/2010 | Odajima et al. |
| 7,713,314 | B2 | 5/2010 | Jones |
| 7,731,767 | B2 | 6/2010 | Tao |
| 7,767,299 | B2 | 8/2010 | Easter |
| 7,833,294 | B2 | 11/2010 | Murphy |
| 7,833,515 | B2 | 11/2010 | Corzani et al. |
| 7,842,746 | B2 | 11/2010 | Bloom |
| 7,959,689 | B2 | 6/2011 | Cagle |
| 8,021,443 | B2 | 9/2011 | Murphy et al. |
| 8,070,833 | B2 | 12/2011 | Murphy |
| 8,070,834 | B2 | 12/2011 | Tao |
| 8,074,605 | B2 | 12/2011 | Hurwitz |
| 8,137,418 | B2 | 3/2012 | Tao |
| 8,157,873 | B2 | 4/2012 | Murphy |
| 8,168,682 | B2 | 5/2012 | O'Connor |
| 8,173,733 | B2 | 5/2012 | Kashihara |
| 8,202,329 | B2 | 6/2012 | Murphy et al. |
| 8,273,826 | B2 | 9/2012 | Walton |
| 8,404,003 | B2 | 3/2013 | Tao et al. |
| 8,439,668 | B2 | 5/2013 | Ambroggio |
| 8,529,924 | B2 | 9/2013 | Murphy et al. |
| 8,551,194 | B2 | 10/2013 | Uptain et al. |
| 8,603,197 | B2 | 12/2013 | Lemke et al. |
| 8,652,221 | B2 | 2/2014 | Uptain et al. |
| 8,685,118 | B2 | 4/2014 | Murphy |
| 8,784,984 | B2 | 7/2014 | Grey |
| 8,940,090 | B2 | 1/2015 | Lemke et al. |
| 9,056,302 | B2 | 6/2015 | Jung et al. |
| 2002/0002792 | A1 | 1/2002 | Freeman et al. |
| 2002/0019510 | A1 | 2/2002 | Orth et al. |
| 2003/0024997 | A1 | 2/2003 | Welch et al. |
| 2003/0105183 | A1 | 6/2003 | Sharak |
| 2003/0195272 | A1 | 10/2003 | Harwell et al. |
| 2004/0146537 | A1 | 7/2004 | Radhakrishnan et al. |
| 2004/0234469 | A1 | 11/2004 | O'Connor et al. |
| 2005/0158679 | A1 | 7/2005 | Chen et al. |
| 2006/0000139 | A1 | 1/2006 | Biggs |
| 2006/0013842 | A1 | 1/2006 | Matkin et al. |
| 2006/0263732 | A1 | 11/2006 | Fiwek |
| 2006/0272199 | A1 | 12/2006 | Licciardello et al. |
| 2007/0006521 | A1 | 1/2007 | Licciardello et al. |
| 2007/0065379 | A1 | 3/2007 | Biatry et al. |
| 2007/0094916 | A1 | 5/2007 | Burkhamer et al. |
| 2007/0108759 | A1 | 5/2007 | D'Amico |
| 2007/0144058 | A1 | 6/2007 | Chen et al. |
| 2007/0169404 | A1 | 7/2007 | Cagle |
| 2007/0282000 | A1 | 12/2007 | Murphy et al. |
| 2008/0132625 | A1 | 6/2008 | Niehaus et al. |
| 2008/0138753 | A1 | 6/2008 | Tao et al. |
| 2008/0282601 | A1 | 11/2008 | Luttke |
| 2008/0292855 | A1 | 11/2008 | Manderfield et al. |
| 2008/0307696 | A1 | 12/2008 | Wu et al. |
| 2009/0041820 | A1 | 2/2009 | Wu et al. |
| 2009/0062427 | A1 | 3/2009 | Tornow |
| 2009/0217568 | A1 | 9/2009 | Murphy et al. |
| 2010/0024281 | A1 | 2/2010 | Lemke et al. |
| 2010/0044924 | A1 | 2/2010 | Cap |
| 2010/0063173 | A1 | 3/2010 | Corzani et al. |
| 2010/0127432 | A1 | 5/2010 | Wagenaar |
| 2010/0205851 | A1 | 8/2010 | Uptain et al. |
| 2010/0212214 | A1 | 8/2010 | Wu et al. |
| 2010/0251671 | A1 | 10/2010 | Thompson et al. |
| 2011/0045424 | A1 | 2/2011 | Litten-Brown et al. |
| 2011/0250151 | A1 | 10/2011 | Mateu et al. |
| 2011/0274643 | A1 | 11/2011 | Yontz |

(56) References Cited

U.S. PATENT DOCUMENTS

| | | |
|---|---|---|
| 2011/0305042 A1 | 12/2011 | Liwei |
| 2012/0015312 A1 | 1/2012 | Kodali |
| 2012/0222347 A1 | 9/2012 | Clock et al. |
| 2013/0012093 A1 | 1/2013 | Bond |
| 2013/0071799 A1 | 3/2013 | Syed et al. |
| 2013/0150458 A1 | 6/2013 | Iyoku |
| 2013/0158169 A1 | 6/2013 | Bond et al. |
| 2013/0178640 A1 | 7/2013 | Mujkic et al. |
| 2013/0270474 A1 | 10/2013 | Cagle |
| 2014/0041525 A1 | 2/2014 | Morrow |
| 2014/0087941 A1 | 3/2014 | Allen, Jr. et al. |
| 2014/0154197 A1 | 6/2014 | Swaile |
| 2014/0199646 A1 | 7/2014 | Beadles |
| 2014/0273169 A1 | 9/2014 | Scheer et al. |
| 2014/0338134 A1 | 11/2014 | Prieto et al. |
| 2014/0360912 A1 | 12/2014 | Constantine et al. |
| 2015/0164920 A1 | 6/2015 | Soler Ranzani et al. |
| 2017/0182198 A1* | 6/2017 | Vazquez Alvarez ...... A61L 9/03 |
| 2017/0209611 A1* | 7/2017 | Banco ...................... A61L 9/012 |

FOREIGN PATENT DOCUMENTS

| | | |
|---|---|---|
| EP | 706790 B1 | 7/1997 |
| EP | 745371 B1 | 12/1997 |
| EP | 1023890 A1 | 8/2000 |
| EP | 0953335 B1 | 1/2002 |
| EP | 1024785 B1 | 1/2003 |
| EP | 1343454 A2 | 9/2003 |
| EP | 1417951 A1 | 5/2004 |
| EP | 1561451 A1 | 8/2005 |
| EP | 1661974 A1 | 5/2006 |
| EP | 1671614 A1 | 6/2006 |
| EP | 1556313 B1 | 12/2006 |
| EP | 1813267 A1 | 8/2007 |
| EP | 1455722 B1 | 1/2008 |
| EP | 2020993 A2 | 2/2009 |
| EP | 2030609 A2 | 3/2009 |
| EP | 1903892 B1 | 4/2009 |
| EP | 0906381 B2 | 7/2009 |
| EP | 1651182 B1 | 11/2009 |
| EP | 1345632 B1 | 2/2010 |
| EP | 1660027 B1 | 2/2010 |
| EP | 2173548 A1 | 4/2010 |
| EP | 1791532 B1 | 5/2010 |
| EP | 1284128 B2 | 7/2010 |
| EP | 2371919 B1 | 6/2012 |
| EP | 2309987 B1 | 8/2012 |
| EP | 1942875 B1 | 8/2015 |
| EP | 1974030 B1 | 9/2016 |
| ES | 2328344 T3 | 11/2009 |
| GB | 1351594 A | 5/1974 |
| GB | 2029836 A | 3/1980 |
| GB | 2199246 A | 7/1988 |
| GB | 2419599 A | 5/2006 |
| GB | 2420348 A | 5/2006 |
| WO | 8906269 A1 | 7/1989 |
| WO | WO9931206 A1 | 6/1999 |
| WO | WO9931207 A1 | 6/1999 |
| WO | 0001416 A1 | 1/2000 |
| WO | 0108872 A1 | 2/2001 |
| WO | 2001083656 A1 | 11/2001 |
| WO | WO03022979 A1 | 3/2003 |
| WO | 2010116385 A2 | 10/2010 |
| WO | 2010125342 A2 | 11/2010 |
| WO | 2010143207 A1 | 12/2010 |
| WO | 2011028744 A1 | 3/2011 |
| WO | 2011030351 A2 | 3/2011 |
| WO | 2011079163 A1 | 6/2011 |
| WO | 2011089395 A1 | 7/2011 |
| WO | 2015026906 A1 | 2/2015 |

OTHER PUBLICATIONS

International Search Report and Written Opinion, International Application No. PCT/US2017/036945, dated Oct. 19, 2017, 10 pages.

Pervais et al., "Development of Novel Wax-enabled Thermoplastic Starch Blends and Their Morphological, Thermal and Environmental Properties," International Journal of Composite Materials, vol. 4, No. 5, 2014, XP002768375. p. 204-p. 212.

Schroeder, "New Developements in Twin Screw Compounding", Coperion, Bulk Solids Handling & Extrusion Seminars, Riyadh & Dubai, Apr. 2013, 49 pages.

International Search Report issued in corresponding International Application No. PCT/US2017/014496, dated Mar. 31, 2017, 4 pages.

Written Opinion of the International Search Authority issued in corresponding International Application No. PCT/US2017/014496, dated Mar. 31, 2017, 6 pages.

* cited by examiner

WAX MELT WITH FILLER

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure generally relates to a wax melt for use in a wax warmer, and more specifically, to a composition for wax melts.

2. Description of the Background of the Invention

Typical wickless candle solutions include an electric warmer or a tea candle heated warmer and a plurality of wax beads designed to be heated therein. The wax beads are usually provided in a container or bag that requires the consumer to tilt and/or pour the wax beads into the warmer. The wax beads are frequently very small and may be susceptible to spilling during this process. Further, consumers frequently must purchase a significant quantity of wax beads to provide the same fragrancing benefits as a traditional candle due to the smaller size of the beads.

In other instances, a typical wickless candle solution includes a warmer and one or more wax melts. The wax melts are usually paraffin or vegetable based. Further, typical wax melts are designed to have a reasonably long shelf life so that the wax melts can be produced, shipped, and positioned in a store for future sale. To make typical wax melts, the components, including any stabilizers, are heated and blended together. After blending, the molten composition is sprayed into beads and pressed into a mold to form the wax melt. This process is typically referred to as compression molding.

The composition of wax melts typically includes a wax substrate (e.g., a paraffin wax or a vegetable wax such as soy wax), a fragrance oil, and a dye. When the dye is present in the composition, color stabilizers are also often added to the composition. The amount of fragrance oil found in wax melts generally falls between 3% and 8% of the total composition by weight. Many consumers wish for greater fragrance strength and/or a longer duration of the fragrance experience than typical wax melts provide. Increasing the percentage of fragrance oil in the wax melt is one way to increase fragrance strength and the length of time over which fragrance is noticeable. However, fragrance oil is generally the most expensive ingredient in a wax melt composition, so it must be used cost-effectively. Furthermore, the amount of fragrance oil that can be added to a wax-based composition has practical limits. For example, high loadings of fragrance oil in wax-based compositions (levels above 8% could be considered "high" by marketplace standards) can lead to syneresis, the bleeding of fragrance oil from the wax substrate.

Therefore, a need exists for a wax melt that provides greater fragrance strength for longer periods of time.

SUMMARY OF THE INVENTION

The present disclosure overcomes some of the aforementioned drawbacks by providing a wax melt that includes a wax substrate, a fragrance oil, and a filler that affects the release rate of the fragrance oil into the atmosphere.

According to one aspect, a wax melt includes between about one and about sixty percent by weight of paraffin wax, between about 3 percent and about 20 percent by weight of fragrance, and between about 10 percent and about 35 percent by weight of a silicate. The silicate causes between about 97 percent and about 98 percent of a wax melt weight to be retained over a time period of about sixteen hours when maintained at about sixty-five degrees Celsius.

According to another aspect, a wax melt includes between about 30 percent and about 60 percent by weight of paraffin wax, between about 3 percent and about 20 percent by weight of fragrance, and between about 10 percent and about 35 percent by weight of a starch. The starch causes between about 94 percent and about 96 percent of a wax melt weight to be retained over a time period of about sixteen hours when maintained at about sixty-five degrees Celsius.

According to a different aspect, a wax melt includes between about 30 percent and about 60 percent by weight of paraffin wax, between about 3 percent and about 20 percent by weight of fragrance, and between about 10 percent and about 35 percent by weight of a structural filler that has a fulcrum percentage. If the structural filler percentage is above the fulcrum percentage, less than 96.9 percent of a wax melt weight is retained over sixteen hours when maintained at about sixty-five degrees Celsius. If the structural filler percentage is below the fulcrum percentage, greater than 96.9 percent of the wax melt weight is retained over sixteen hours when maintained at about sixty-five degrees Celsius.

BRIEF DESCRIPTION OF THE DRAWINGS

Other aspects and advantages of the present invention will become apparent upon consideration of the following detailed description, wherein similar structures have similar reference numerals.

DETAILED DESCRIPTION

The delivery rate of a fragrance or other volatile material from a heated wax melt can be modulated by the addition of solid fillers to the wax melt composition. Generally, a fragrance as used herein refers to any volatile material that provides a functional benefit and can be delivered from a heated wax substrate. Numerous filler materials can be combined with wax to modulate the fragrance delivery rate. The following description describes the effect of three different exemplary fillers, and describes several non-limiting examples of the effects caused by different concentrations in a wax melt composition. Percentages discussed in this application, unless noted or used otherwise, refer to percentages by weight of a total wax melt weight.

In preferred embodiments, the filler chosen to be incorporated with the wax will have the following characteristics: (i) the filler will modulate a release rate of a fragrance from a wax melt; (ii) the filler will yield a composition that maintains the appearance and feel of wax both before and after melting in a warmer dish; and (iii) the filler allows a used-up wax melt (cooled in the warmer dish) to be easily removed from the warmer dish.

As noted above, the filler may be used to increase or decrease the release rate of fragrance from the wax melt, which may be characterized as the percentage change in weight of the fragrance in the wax melt over time. Different products may have different optimal release rates, which means that changing the type or quantity of the filler can affect the release rate such that targeted products can be produced. For example, a fast release wax melt may be desirable for quickly dispersing fragrance into a room before a party. Alternatively, aromatherapy wax melts may desirably provide a subtle and long lasting fragrance. Generally, compositions that include a filler intended to increase or decrease the release rate of fragrance can be referred to as time release fragrance compositions.

Figure 1:
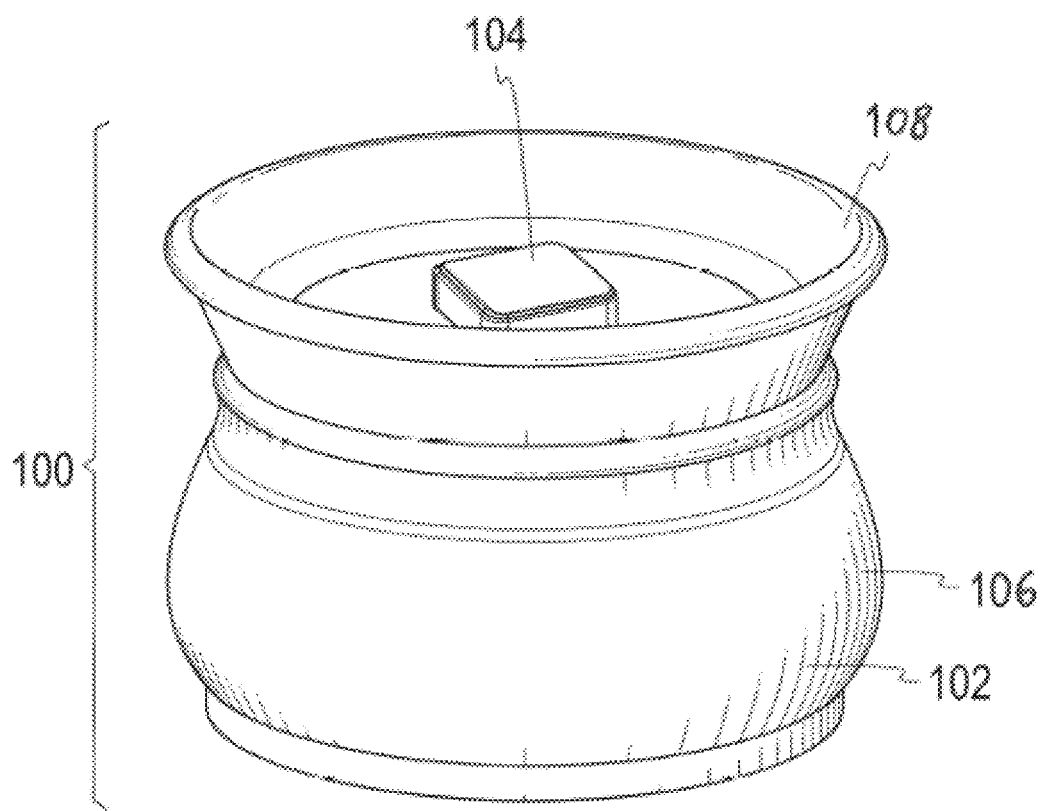
FIG. 1 is a perspective view of a wax melt system according to one embodiment.

FIG. 1 shows a wax melt system 100 that includes a warmer 102 for melting a wax melt 104. The warmer 102 includes a body 106 and a reservoir 108. The illustrated warmer 102 is an electric warmer that provides heat to the reservoir 108 via an electric element. In other embodiments, the reservoir 108 may be heated by a tea candle or another heat source.

Fillers or time release fillers within the context of this application provide a modification or modulation of the release rate of a fragrance entrained within a wax substrate. The release rate of a fragrance is defined as a weight reduction of the wax melt 104 over time while heated by a warmer 102. Categories of fillers include silicates, starches, and structural fillers. Alternatively, fillers may be plant-based (e.g., starches, sugars, or wood flour) or mineral-based. Further, fillers may be classified as either hydrophobic, hydrophilic, lipophobic, or lipophillic. Additionally, fillers may be classified by surface area. Generally, it is preferred to include between about ten percent and thirty percent (10-30%) by weight of filler.

The addition of silicates tends to decrease the release rate of the fragrance. That is to say, the percentage of silicates within the wax melt composition is inversely proportional to the release rate. The addition of starches tends to increase the release rate of the fragrance. That is to say, the percentage of starches within the wax melt composition is proportional to the release rate. The addition of structural fillers can be used to either increase or decrease the release rate of the fragrance. Each individual structural filler, or subcategory of structural filler, defines a fulcrum percentage. A percentage above the fulcrum percentage will increase the release rate of the fragrance, and a percentage below the fulcrum percentage will decrease the release rate.

The filler used can also affect the level of fragrance loading that a particular wax melt can accept. For example, the inclusion of talc in the wax melt increases the fragrance loading of a wax melt without introducing or increasing problems due to syneresis. In other words, a wax melt that includes talc can accept more fragrance without experiencing syneresis when compared to a wax melt without talc. In one trial, a wax melt with 10% by weight of talc was able to accept 12% by weight of fragrance as opposed to a wax melt with no filler only accepting up to 8% of fragrance by weight.

Additionally, fillers effect the appearance, function, and production of wax melts. Preferably, a wax melt should feel like pliable wax, melt completely during warming, and release cleanly from a warmer reservoir once cooled after use. Generally, as the amount of filler increases, a wax melt will become more stiff. Exceeding a brittleness threshold percentage can lead to a wax melt that appears brittle, does not feel like wax in a user's hand, and/or will not melt completely. Above the brittleness threshold percentage, the wax melt will fracture if compressed in a user's hand. Below the brittleness threshold percentage, the wax melt will plastically deform if compressed in a user's hand. In one example, the brittleness threshold percentage is about 50% by weight of a silicate such as talc. In another example, the brittleness threshold percentage is about 80% by weight of a starch such as corn starch. In another example, the brittleness threshold percentage is about 25% by weight of a structural filler such as wood flour.

Additionally, the amount of filler can affect ease of production. For example, a wax melt produced using a twin screw extrusion process may benefit from a filler that increases the stiffness of the wax melt. Such an effect may lead to a more pleasing surface finish of the finished wax melt. The balance of brittleness and surface finish leads to a preferred structural range of filler percentages that lead to a non-brittle and visually attractive wax melt. In one example, a wax melt including a silicate filler preferably includes between about 20% and about 25% percent by weight of a silicate filler. In another embodiment, a wax melt including a starch filler preferably includes between about 25% and about 30% percent by weight of a starch filler. In a different embodiment, a wax melt including a structural filler preferably includes between about 15% and about 20% percent by weight of a structural filler.

EXAMPLES

Experiments were conducted where several wax melt compositions were created and a thermogravimetric analysis (TGA) was conducted on each composition. Talc (i.e., a silicate), corn starch (i.e., a starch), and wood flour (i.e., a structural filler) were each included at 5% and 20% in a mixture with paraffin wax and fragrance oil. In the tests, a sample was ramped in temperature by 30° C./min from room temperature to a holding temperature of 65° C. The temperature of 65° C. was held for 16 hours. The following plots were generated showing the percentage weight of a fragrance in the wax melt over time.

Figure 2:
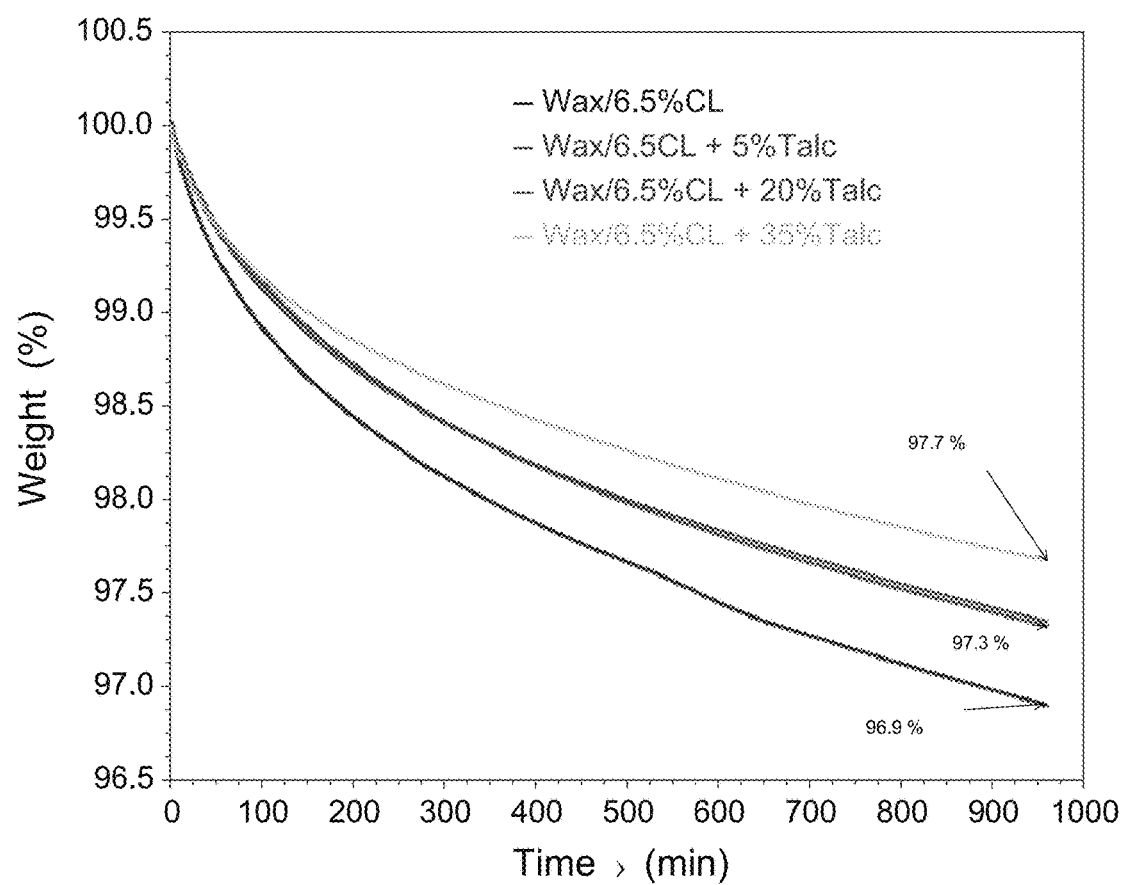
FIG. 2 is a graph showing test results of wax melt testing using a silicate filler.

FIG. 2 shows the results of a test run with the addition of talc (0%, 5%, 20%, and 35% by weight) to a paraffin wax and fragrance oil mixture (constant at 6.5%). In general, the talc slowed the release rate of fragrance when the wax melt was heated to 65° C. Over the course of the test, the control wax melt that included 0% talc maintained about 96.9% of its weight. The samples that included talc all showed significant decreases in release rate. The 5% and 20% talc by weight samples both maintained about 97.3% of initial weight and the sample with 35% of talc by weight maintained about 97.7% of initial weight. It was experimentally determined that the addition of talc and other silicates can be used to decrease the release rate of fragrance in wax melts.

Figure 3:
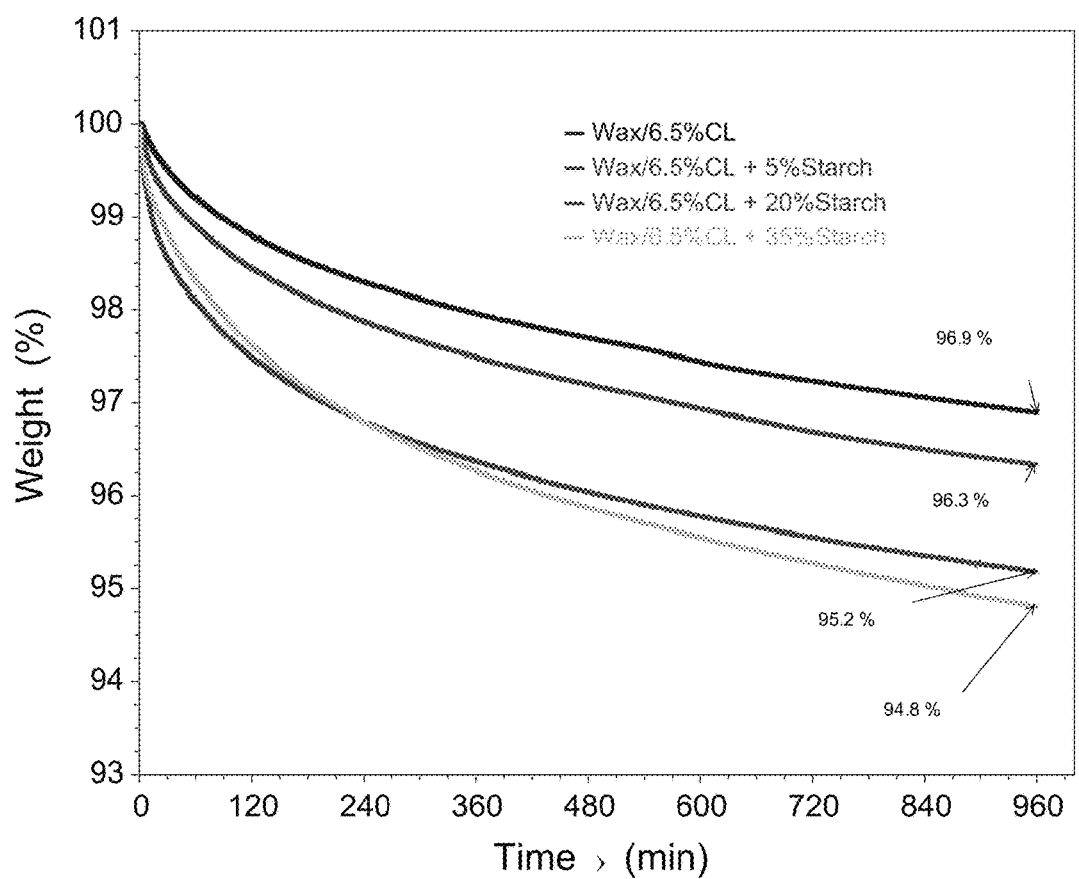
FIG. 3 is a graph showing test results of wax melt testing using a starch filler.

FIG. 3 shows the results of a test run with the addition of corn starch (0%, 5%, 20%, and 35% by weight) to a paraffin wax and fragrance oil mixture (constant at 6.5%). In general, the corn starch increased the release rate of fragrance when the wax melt was heated to 65° C. Over the course of the test, the control wax melt that included 0% corn starch maintained about 96.9% of its weight. The samples that included corn starch all showed significant increases in release rate. The 5% corn starch by weight sample maintained about 96.3% of initial weight, the 20% corn starch by weight sample maintained about 95.2% of initial weight, and the sample with 35% of corn starch by weight maintained about 94.8% of initial weight. It was experimentally determined that the addition of corn starch and other starches can be used to increase the release rate of fragrance in wax melts.

Figure 4:
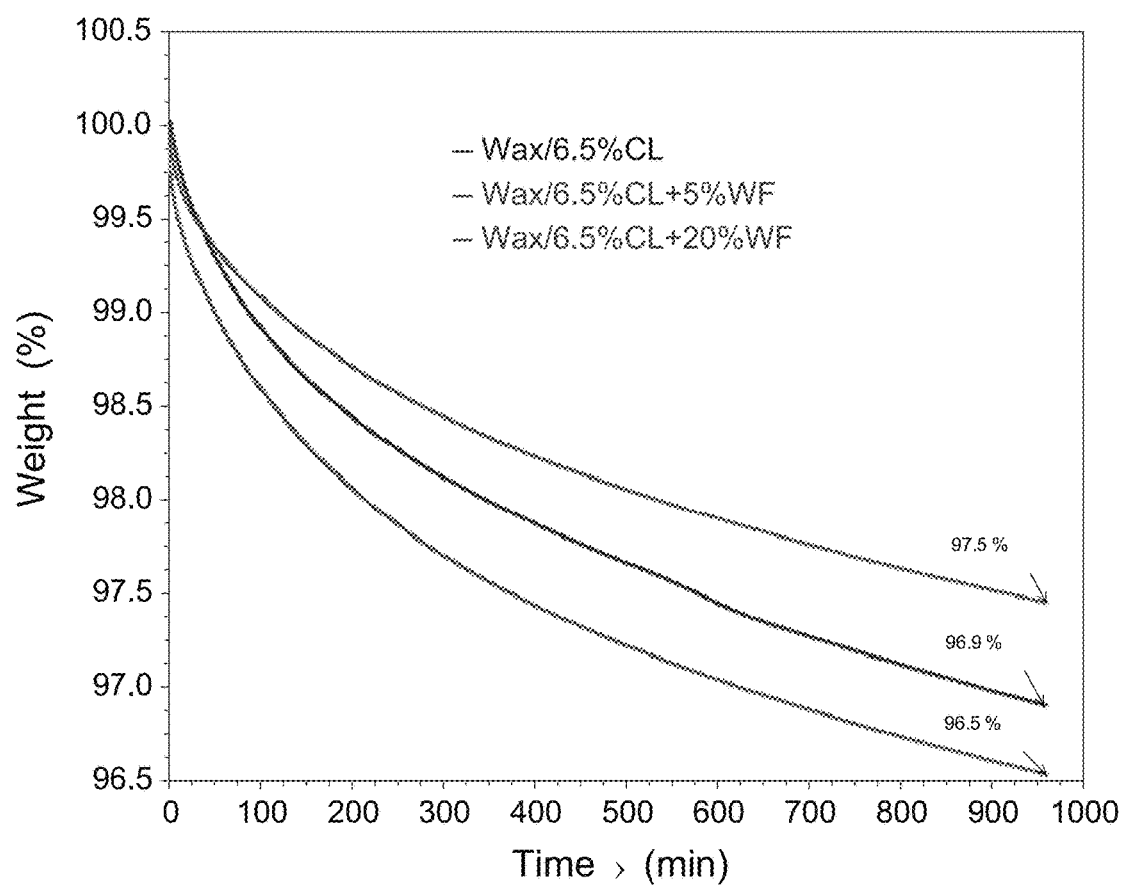
FIG. 4 is a graph showing test results of wax melt testing using a structural filler.

FIG. 4 shows the results of a test run with the addition of wood flour (0%, 5%, and 20%) to a paraffin wax and fragrance oil mixture (constant at 6.5%). It was found that the amount of wood flour used in the composition affected whether the release rate of the fragrance was increased or decreased. A wax melt including 20% wood flour by weight increased the release rate of fragrance from the wax melt. The wax melt including 20% of wood flour by weight maintained about 96.5% of initial weight. A wax melt including 5% wood flour by weight decreased the release rate of fragrance from the wax melt. The wax melt including 5% wood flour by weight maintained about 97.5% of initial weight. Therefore, the inclusion of a structural filler above a fulcrum percentage can raise the fragrance release rate, and the inclusion of a structural filler below a fulcrum percentage can decrease or limit the fragrance release rate.

The results for these three fillers (talc, wood flour, and corn starch) show that the delivery rate of fragrance from a wax melt composition can be modulated either up or down with the addition of a filler. Talc slowed down the fragrance delivery rate at both 5% and 20% loadings. Corn starch accelerated fragrance delivery rates at 5% and 20% loadings. Wood flour slowed fragrance delivery rates at a 5% loading, but accelerated fragrance delivery rate at a 20% loading. The discovery that fillers can be used to modulate the delivery of functional materials from a heated wax composition is useful. For example, if the volatile material is a fragrance, consumers may be given a more intense fragrance experience if fillers are used that accelerate fragrance delivery rates.

One exemplary composition includes about 57% paraffin wax, about 10% microcrystalline wax, about 25% cornstarch, less than 1% octabenzone, about 7% fragrance, and a small amount of dye.

Any of the embodiments described herein may be modified to include any of the structures or methodologies disclosed in connection with different embodiments. Further, the present disclosure is not limited to wax warmers, wax melts, or extrusion machines of the type specifically shown and described. Still further, the wax melts of any of the embodiments disclosed herein may be modified to work with any type of warmer that utilizes wax melts or the like.

INDUSTRIAL APPLICABILITY

A wax melt is presented that is heated by a wax warmer for dispensing material into the surrounding environment. The wax melt includes a filler that affects the release rate of the dispensed material while providing a wax melt that appears desirable and can be easily removed from a wax warmer reservoir.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A wax melt, comprising:
   between about 30 percent and about 60 percent by weight of paraffin wax;
   between about 3 percent and about 20 percent by weight of fragrance; and
   between about 10 percent and about 35 percent by weight of wood flour.

2. The wax melt of claim 1, wherein the paraffin wax comprises about 57 percent by weight.

3. The wax melt of claim 2 further comprising about 10 percent by weight of microcrystalline wax.

* * * * *